United States Patent
Chen

(10) Patent No.: US 11,266,478 B2
(45) Date of Patent: Mar. 8, 2022

(54) SURGICAL BOWL SET

(71) Applicant: Multigate Medical Products Pty Ltd, Villawood (AU)

(72) Inventor: Ben Chen, Villawood (AU)

(73) Assignee: Multigate Medical Products Pty Ltd, Villawood (AU)

(*) Notice: Subject to any disclaimer, the term of this patent is extended or adjusted under 35 U.S.C. 154(b) by 0 days.

(21) Appl. No.: 15/750,045

(22) PCT Filed: Aug. 3, 2016

(86) PCT No.: PCT/AU2016/050700
§ 371 (c)(1),
(2) Date: Feb. 2, 2018

(87) PCT Pub. No.: WO2017/020083
PCT Pub. Date: Feb. 9, 2017

(65) Prior Publication Data
US 2019/0060024 A1 Feb. 28, 2019

(30) Foreign Application Priority Data
Aug. 3, 2015 (AU) .................................. 2015903094

(51) Int. Cl.
| B65D 21/02 | (2006.01) |
| A61B 50/37 | (2016.01) |
| A61B 50/30 | (2016.01) |
| A61B 50/36 | (2016.01) |
| A61B 50/39 | (2016.01) |

(52) U.S. Cl.
CPC .............. *A61B 50/37* (2016.02); *A61B 50/30* (2016.02); *A61B 50/36* (2016.02); *A61B 50/362* (2016.02); *A61B 50/39* (2016.02); *A61B 2050/3006* (2016.02); *A61B 2050/375* (2016.02)

(58) Field of Classification Search
CPC ......... A61B 50/37; A61B 50/30; A61B 50/36; A61B 50/362; A61B 50/39; B65D 81/3216; B65D 21/0233; B65D 2543/00731
USPC .............. 206/370, 504, 438; 220/23.83, 23.4
See application file for complete search history.

(56) References Cited

U.S. PATENT DOCUMENTS

| 3,117,692 A | * | 1/1964 | Carpenter | .......... B65D 21/0219 |
| | | | | 206/501 |
| 3,589,554 A | * | 6/1971 | Smith | ................ B65D 81/3216 |
| | | | | 220/23.83 |

(Continued)

FOREIGN PATENT DOCUMENTS

| AU | 362536 | 7/2015 |
| AU | 362537 | 7/2015 |

(Continued)

*Primary Examiner* — King M Chu
(74) *Attorney, Agent, or Firm* — Mark Malek; Widerman Malek, PL

(57) ABSTRACT

A surgical bowl set features a first rectilinear bowl having an internal length (1*l*) and an internal width (1*w*), and a second rectilinear bowl having an external length (2*l*) and an external width (2*w*), in which the external length (2*l*) is close to but less than internal length (1*l*) in order to permit the second bowl to fit lengthwise within the first bowl while allowing easy extraction of the second bowl from the first bowl, and the external width (2*w*) is about half or less of internal width (1*w*).

10 Claims, 6 Drawing Sheets

(56) References Cited

U.S. PATENT DOCUMENTS

| | | | | |
|---|---|---|---|---|
| 8,006,839 B2* | 8/2011 | Hafner | .................. | A61B 50/30 |
| | | | | 206/363 |
| 2009/0145797 A1* | 6/2009 | Steinmeyer | ........ | B65D 21/0233 |
| | | | | 206/507 |
| 2011/0290796 A1* | 12/2011 | Burgess | ................ | B65D 21/04 |
| | | | | 220/23.2 |
| 2015/0021321 A1* | 1/2015 | Gosen | .................. | B65D 43/021 |
| | | | | 220/23.83 |

FOREIGN PATENT DOCUMENTS

| | | |
|---|---|---|
| AU | 362538 | 7/2015 |
| AU | 362540 | 7/2015 |
| GB | 1203403 | 8/1970 |

\* cited by examiner

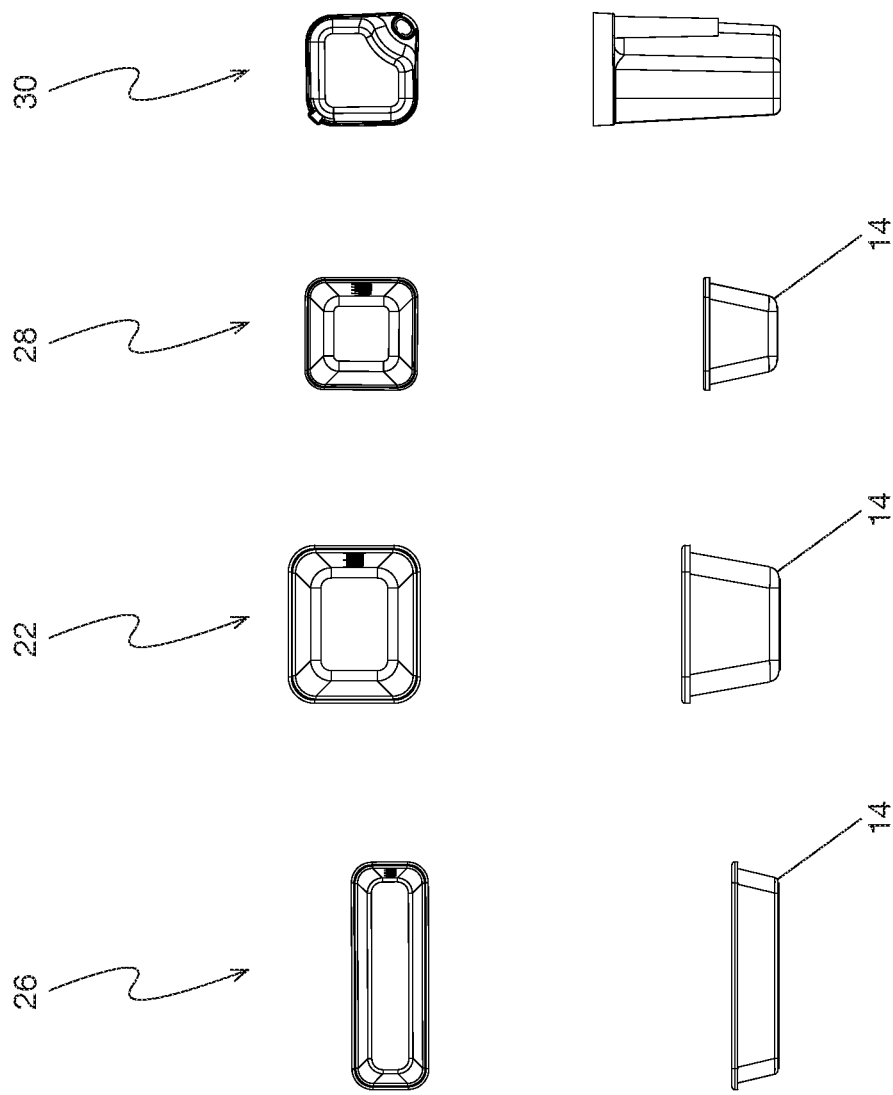

SURGICAL BOWL SET

TECHNICAL FIELD

The present invention relates to surgical bowls.

BACKGROUND ART

Surgical bowls are used as receptacles in surgical theatres in many ways. For example, surgical bowls may be used to collect fluids, such as blood, or specimens, such as kidney stones, during surgery. Surgical bowls may hold antiseptic or washing fluids in preparation for surgery. A surgical bowl may be used to hold a skin graft taken from a donor site before being attached to the recipient site. Surgical bowls are furthermore used to transfer instruments between personnel, to minimise injury, and can be used as a receptacle for used instruments, such as scalpels, or bloodies sponges or swabs.

The following references to and descriptions of prior proposals or products are not intended to be, and are not to be construed as, statements or admissions of common general knowledge in the art. In particular, the following prior art discussion does not relate to what is commonly or well known by the person skilled in the art, but assists in the understanding of the inventive step of the present invention of which the identification of pertinent prior art proposals is but one part.

Existing surgical bowls are provided in various sizes, depending on their intended use. The largest bowl may be 7 to 8 litres in capacity; the smallest may be about 400 ml.

Surgical bowls take one of two shapes: round or kidney-shaped. Such surgical bowls may be nested, smaller within larger, but a nested combination of round bowls, or of kidney bowls, do not represent an efficient shape for sterilisation, storage or use, especially when a varying combination of surgical bowls are required for different surgical procedures.

An object of the present invention, at least in preferred embodiments, is to provide a surgical bowls which can ameliorate the disadvantages of the prior art or to at least provide a useful alternative thereto.

SUMMARY OF INVENTION

Particular technical problems addressed by embodiments of the present invention relate to provision of a varying combination of surgical bowls in a form which is space efficient, and moreover permits advantageous use during surgery. These technical problems represent an unmet need in the art, inadequately addressed by existing solutions.

The foregoing technical problems are addressed by embodiments of the present invention, as outlined below.

The present invention in a first aspect provides a surgical bowl set including:

a first rectilinear bowl having an internal length $1l$ and an internal width $1w$; and a second rectilinear bowl having an external length $2l$ and an external width $2w$;

wherein external length $2l$ is close to but less than internal length $1l$ in order to permit the second bowl to fit lengthwise within the first bowl while allowing easy extraction of the second bowl from the first bowl; and wherein external width $2w$ is about half or less of internal width $1w$.

The present invention in a second aspect provides a surgical bowl set including:

a first rectilinear bowl having an internal length $1l$ and an internal width $1w$; and a third rectilinear bowl having an external length $3l$ and an external width $3w$;

wherein external length $3l$ is about half or less of internal length $1l$; and wherein external width $3w$ is half or less of internal width $1w$.

The first and second aspects of the invention may be combined, as illustrated in the drawings.

For the surgical bowl set of the invention, the first rectilinear bowl preferably has internal width $1w$ being about 75% of internal length $1l$.

The second bowl is preferably oblong in shape, having external width $2w$ being about 33 to 34% of external length $2l$.

The third bowl is preferably closer to square in shape, having external width $3w$ being about 80 to 100% of external length $3l$.

Preferably, the dimensions of the first bowl and those of the second and third bowls are such that the first bowl can accommodate:

two second bowls, side by side, with enough difference in internal length $1l$ and external length $2l$ to enable each second bowl to be easily removed from the first bowl;

one second bowl and one third bowl, side by side; or one second bowl and two third bowls, the third bowls being received within internal length $1l$ and each being beside the second bowl.

Each bowl in a surgical bowl set may have a base and upstanding walls. Preferably, the walls taper outwardly towards the bowl opening.

Each or some of the bowls in a surgical bowl set of the invention may have a flange around some or all of its opening.

Each or some of the bowls in a surgical bowl set of the invention may be of at least two differing heights.

When measuring external length, it is preferred to take into account any such flange. However, when measuring external width, any flange need not necessarily be taken into account. The reason is that second, third and subsequent bowls in a surgical bowl set of the invention may be provided in different heights, so that a flange of one bowl may overlap with the flange of another collocated bowl, without impeding fit of the bowls within the first bowl of the surgical bowl set.

Otherwise, external length and width measurements should be taken at the base or at the top.

Each of the second and third bowls may receive one or more nested further bowls. Preferably, such further bowls echo the shape of the bowl in which they nest, but on a smaller scale.

The surgical bowl set of the invention may also receive a jug or other rectilinear item, useful in surgical procedures.

Advantageous effects of embodiments of the present invention are manifold.

Surgical bowl sets provided in accordance with embodiments of the present invention can—more specifically—realise particular technical advantages not associated with existing surgical bowls, including an optimum number of bowls, stacked efficiently, to minimise space required during shipping, storage, and sterilisation, and during use.

These advantages are particularly compelling as different surgical bowl size combinations are required for different surgical procedures. An ability to provide surgical bowl sets which can retain minimal space advantages while providing for a range of different bowl size combinations is particularly advantageous in light of the existing state of the art.

Because the surgical bowl set of the invention has rectilinear bowls, and because of the size relationship between the first bowl and the second and/or third bowls, a bowl set of the invention can represent a most efficient use of space for shipping, storage, sterilisation and use. In addition, the length and width relationship between the respective bowls allows a wide range of combinations of bowls to be included in a single surgical bowl set, to suit individual requirements.

The surgical bowl set of the invention may be intended for single use or multiple uses. The material from which the bowl set of the invention is made may be chosen accordingly. For single use, the bowl set is preferably made from plastic or other suitable material. For multiple uses, the bowl set is preferably stainless steel or other material which can withstand multiple sterilisation cycles. Preferably, the surgical bowl set of the invention is shipped already sterilised.

BRIEF DESCRIPTION OF DRAWINGS

The invention in its two aspects may be better understood from the following non-limiting description of preferred embodiments.

FIG. 6 shows plan and side view elevations of embodiments of third, fifth and sixth bowls and of a jug, all with examples of measurements. A schematic drawing of a networked architecture used to implemented the described platform.

DESCRIPTION OF EMBODIMENTS

Preferred features of embodiments of the present invention will now be described with particular reference to the accompanying drawings. However, it is to be understood that the features illustrated in and described with reference to the drawings are not to be construed as limiting on the scope of the invention.

It will also be appreciated that not all the drawings are on the same scale.

Figure 1:
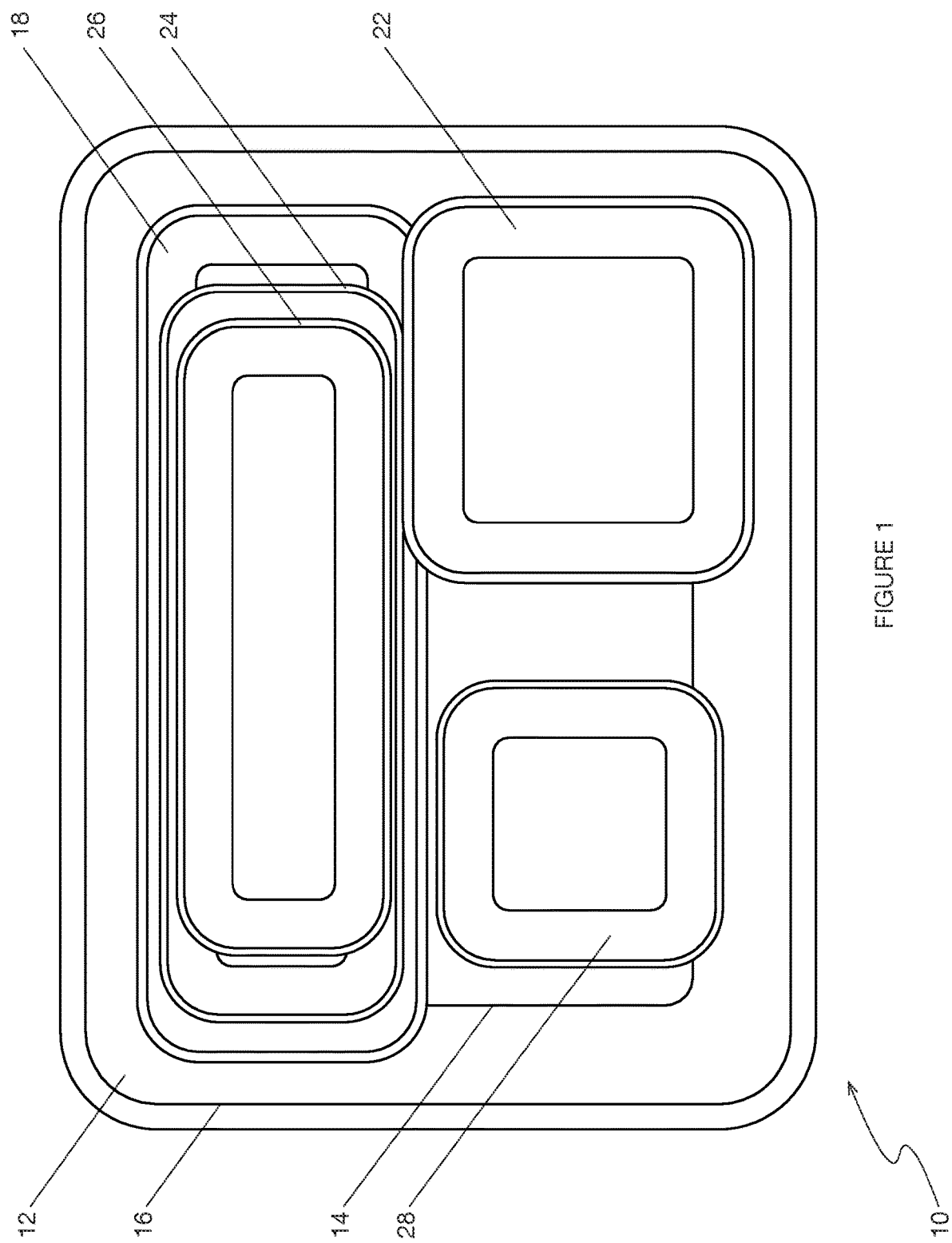
FIG. 1 is a plan view of a first embodiment of a surgical bowl set according to the invention.

Referring to FIG. 1, there is shown a surgical bowl set 10 suitable for use in a surgical procedure. In this embodiment, first rectilinear bowl 12 has an internal length 1*l* and an internal width 1*w* at base 14. An example of internal length at base 14 is 271 mm or 308 mm at top 16, while an example of internal width 1*w* at base 14 is 189 mm or, at top 16, 258 mm. First bowl 12 has a capacity of about 7 to 8 litres.

Second rectilinear bowl 18 is generally oblong in shape. According to FIG. 5, an example of its external length 2*l*, including flange 20, is 290 mm, while an example of its external width 2*w* is 103 mm. External length 2*l* is close to but less than internal length 1*l* in order to permit the second bowl 18 to fit lengthwise within the first bowl 12 while allowing easy extraction of the second bowl 18 from the first bowl 12. External width 2*w* is less than half of internal width 1*w*. Second bowl 18 has a capacity of about 1 litre.

Also shown in FIG. 1 are third bowl 22, fourth bowl 24, fifth bowl 26 and sixth bowl 28. These bowls have a capacity of about 1 litre, 750 ml, 485 ml and 430 ml, respectively.

Second bowl 18 has nested in it fourth and fifth bowls 24 and 26, the three bowls being of similar oblong shape.

According to FIG. 6, an example of length 3*l* for third bowl 22 is 109 mm at base 14 or 152 mm at top 16. An example of width 3*w* is 84 mm at base 14 or 127 mm at top 16. External length 3*l* is about half or less of internal length 1*l*. External width 3*w* is half or less of internal width 1*w*.

Sixth bowl 28 is located in bowl set 10 beside each of second bowl 18 and third bowl 22.

Figure 2:
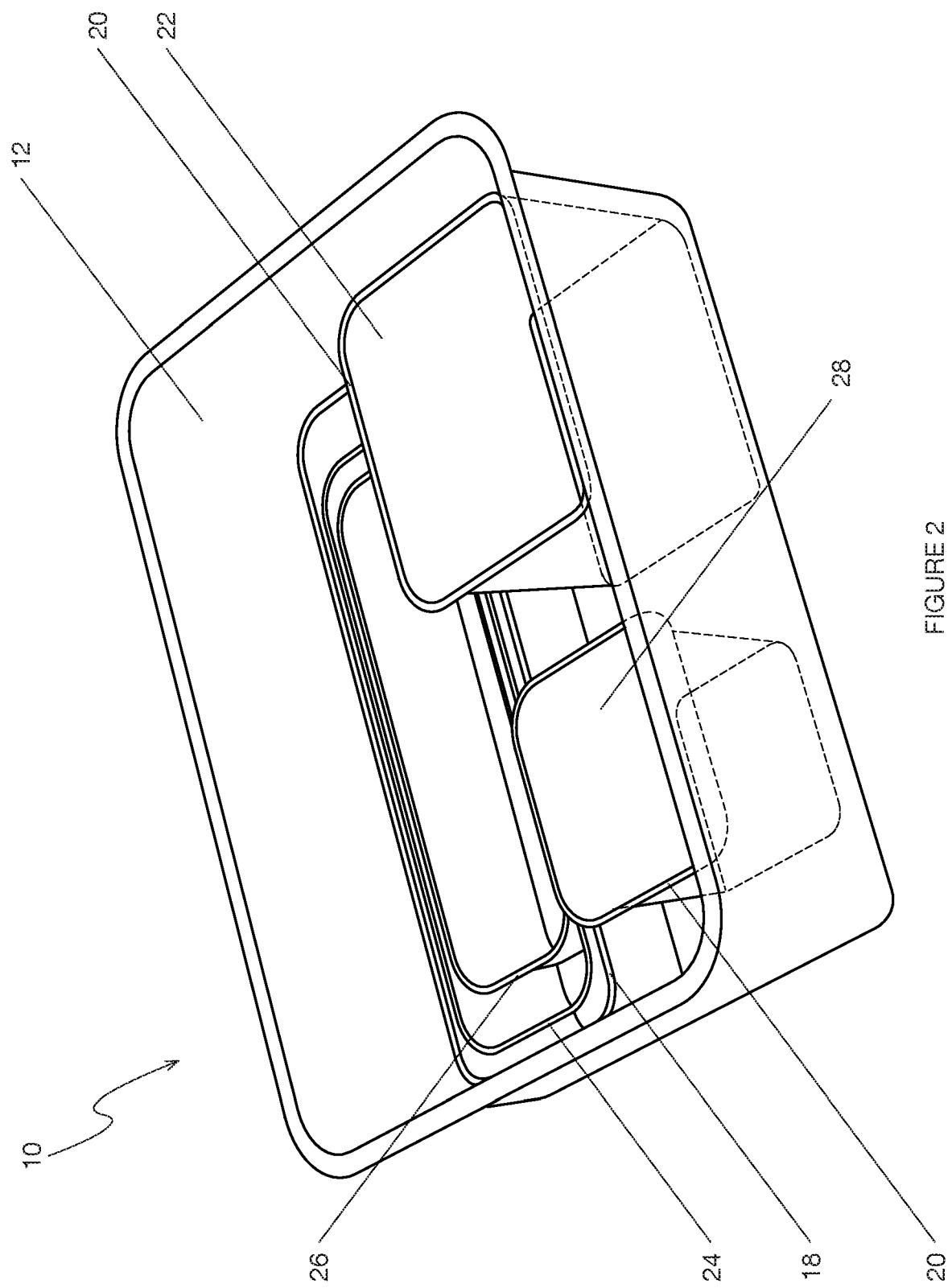
FIG. 2 is a perspective view of the embodiment of FIG. 1.

As shown in FIG. 2, third bowl 22 and sixth bowl 28 are higher than bowls 18, 24 and 26. The flanges 20 of bowls 22 and 28 can overlap with those of bowls 18, 24 and 26.

Figure 3:
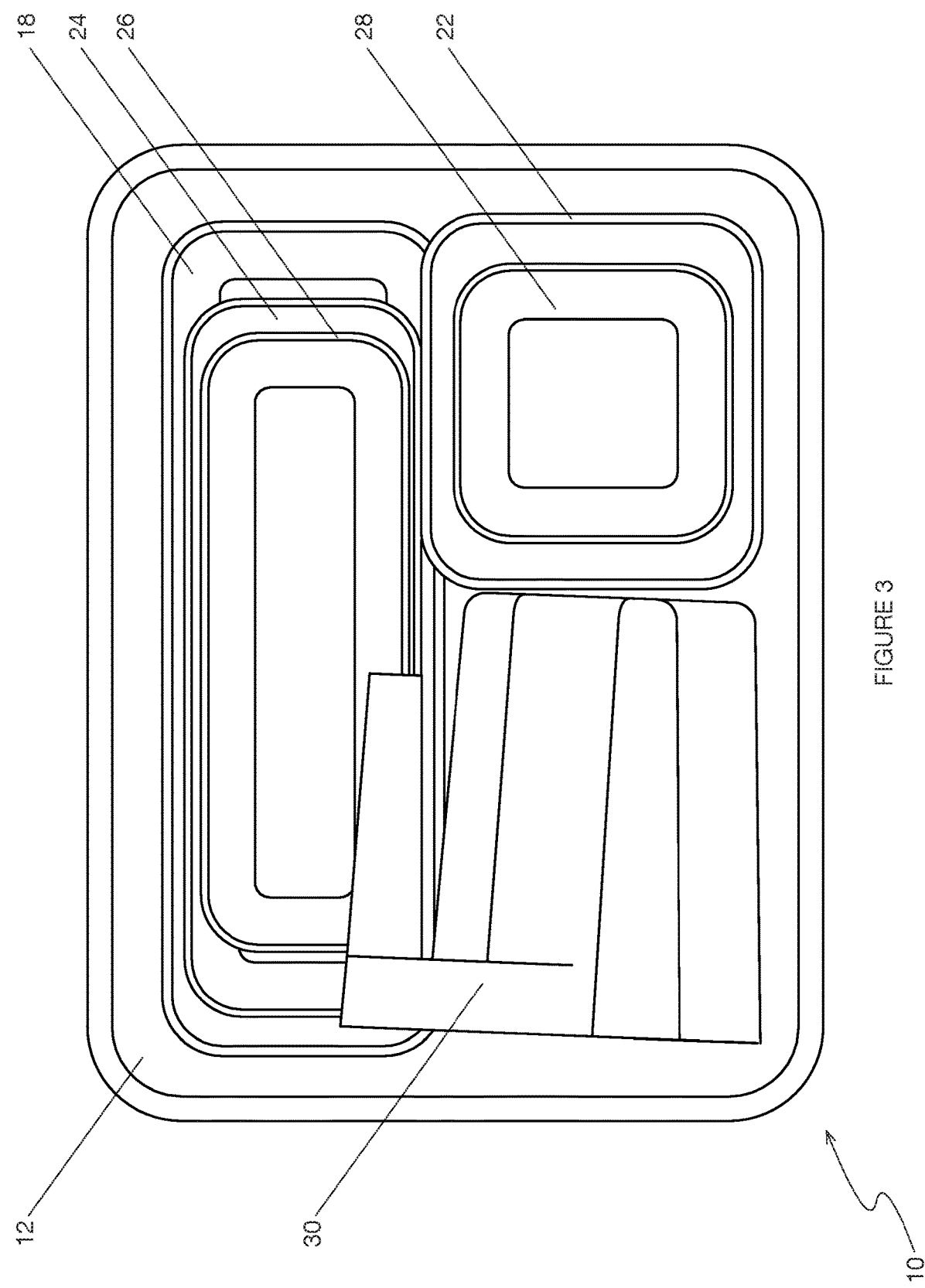
FIG. 3 is a plan view of a second embodiment of a surgical bowl set according to the invention.
Figure 4:
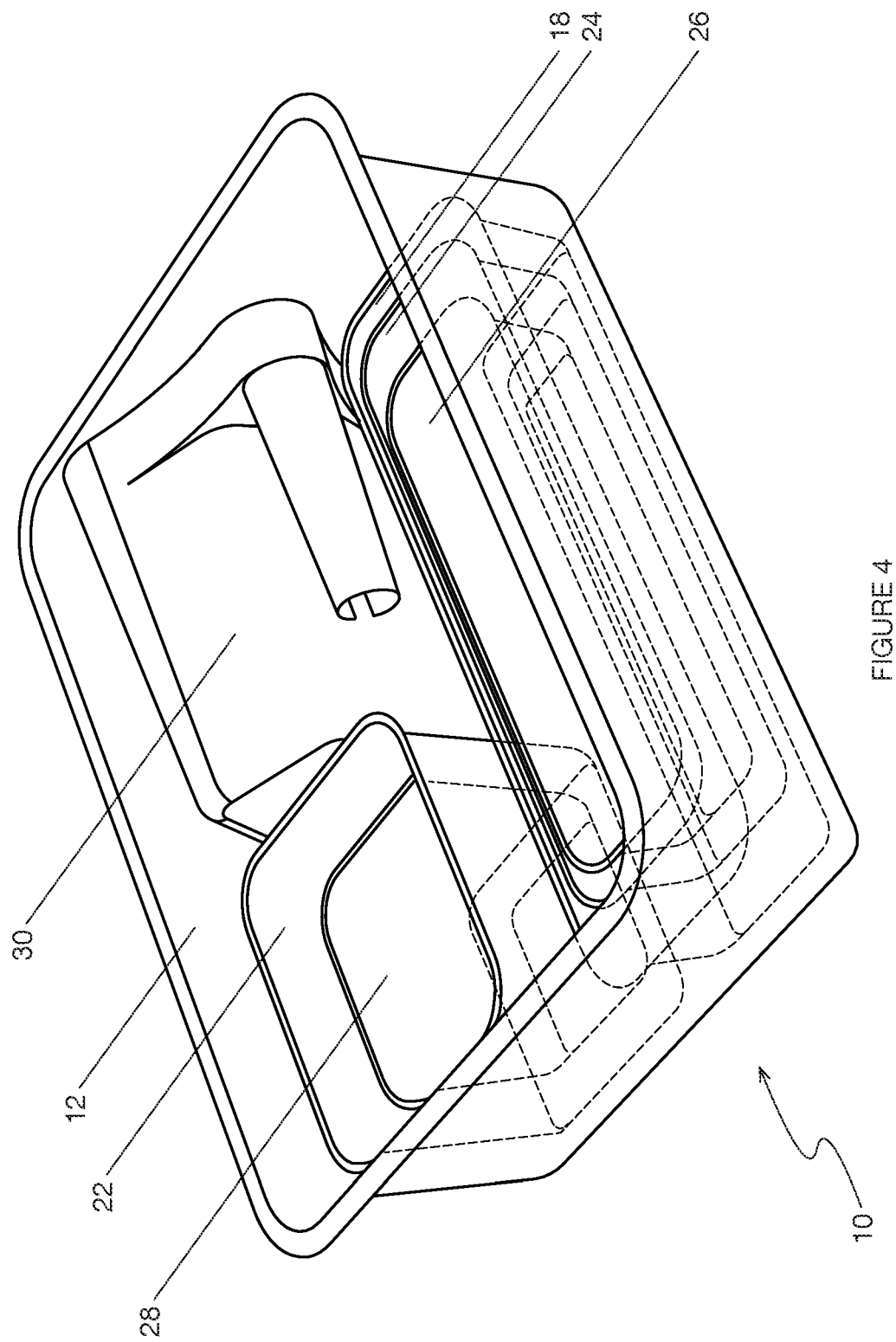
FIG. 4 is a perspective view of the embodiment of FIG. 3.

Turning now to the embodiment depicted in FIGS. 3 and 4, the same first bowl 12 hold bowls 18, 24 and 26 (in a nested configuration). Bowl 28 is nested in bowl 22. The resultant space is occupied by jug 30, which is of rectilinear shape to maximise space advantage (see also FIG. 6).

Figure 5:
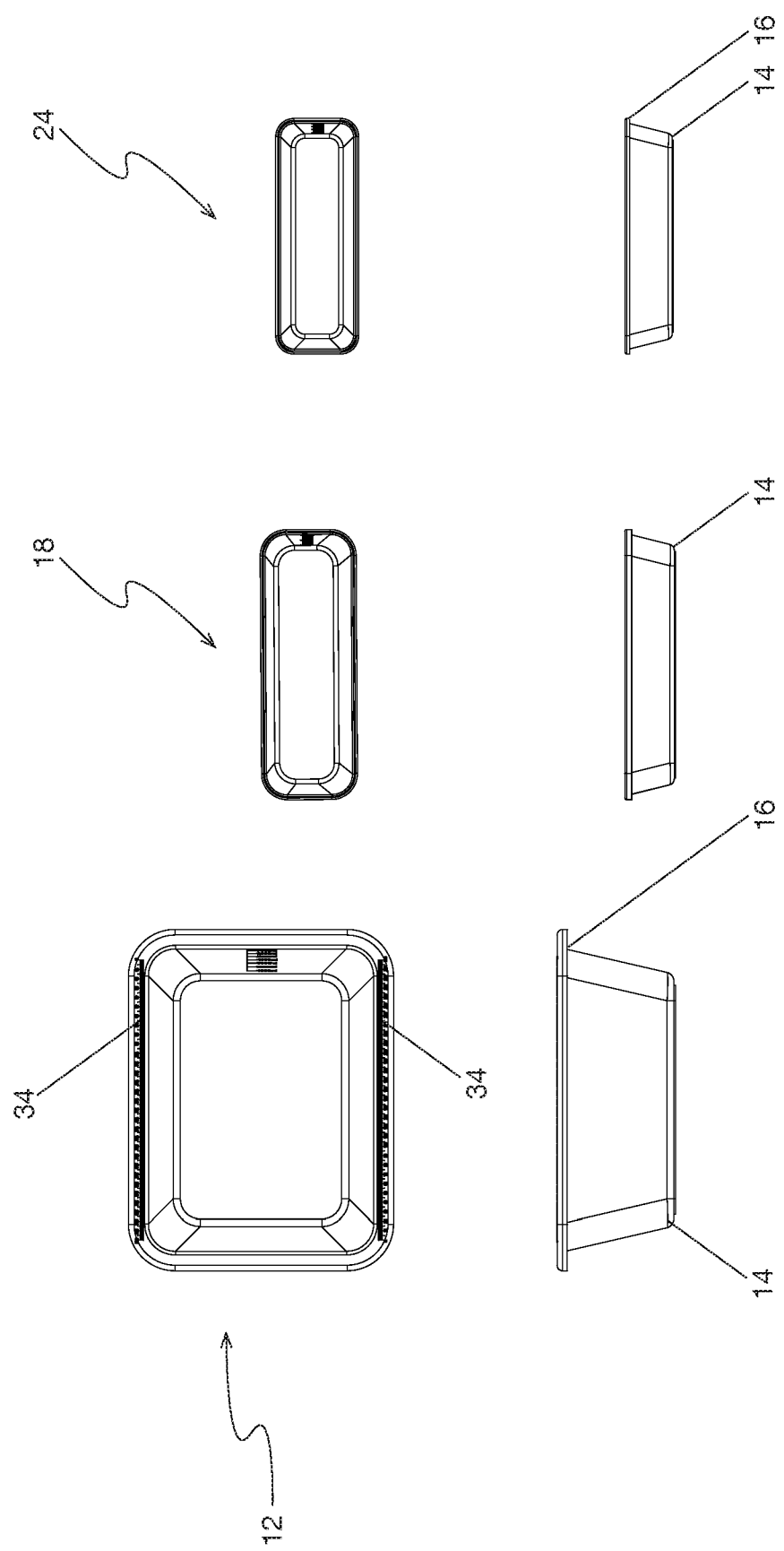
FIG. 5 shows plan and side elevations of embodiments of the first, second and fourth bowls; with examples of measurements.

In FIG. 5 first bowl 12 is shown having a ruler 34 along its length on each of two sides. An example of the purpose of the ruler 34 is to assist in calculating the size of a donor graft which may have been placed in bowl 12, before attachment to the recipient site.

The general shape of jug 30 can be seen in FIG. 6.

Orientational terms used in the specification and claims such as vertical, horizontal, top, bottom, upper and lower are to be interpreted as relational and are based on the premise that the component, item, article, apparatus, device or instrument will usually be considered in a particular orientation.

It will be appreciated by those skilled in the art that many modifications and variations may be made to the methods of the invention described herein without departing from the spirit and scope of the invention.

The invention claimed is:

1. A surgical bowl set including:
   a first rectilinear bowl having an internal length (1*l*) and an internal width (1*w*); and
   a second rectilinear bowl having an external length (2*l*) and an external width (2*w*);
   a third rectilinear bowl having a third external length (3*l*) and a third external width (3*w*);
   wherein the external length (2*l*) is less than the internal length (1*l*) such that the external length (2*l*) is at least fifty percent of the internal length (1*l*) in order to permit the second bowl to fit lengthwise within the first bowl, and an interior surface of a base of the first bowl abuts an exterior surface of the second bowl such that the second bowl is nested within the first bowl;
   wherein the external width (2*w*) is half or less than half of the internal width (1*w*) such that when the surgical bowl set is used in surgery, the second bowl is extractable from the first bowl;
   wherein the third external length (3*l*) is half or less than half of the internal length (1*l*); and
   wherein the third external width (3*w*) is half or less than half of the internal width (1*w*).

2. The surgical bowl set of claim 1, which includes a fourth bowl nested in the second bowl and a fifth bowl nested in the fourth bowl.

3. The surgical bowl set of claim 2, which also contains a sixth bowl that is configured to be nested within the third bowl.

4. The surgical bowl set of claim 1, in which the bowls each have a base and upstanding walls which taper outwardly towards a bowl opening, and a flange around the bowl opening.

5. The surgical bowl set of claim 1, in which the second and third bowls are of different heights, and features flanges that overlap on abutting respective sides.

6. A surgical bowl set including:
- a first rectilinear bowl having an internal length ($1l$) and an internal width ($1w$); and
- a second rectilinear bowl having an external length ($2l$) and an external width ($2w$);
- a third rectilinear bowl having a third external length ($3l$) and a third external width ($3w$);
- wherein external length ($2l$) is half or less than half of internal length ($1l$);
- wherein external width ($2w$) is half or less than half of internal width ($1w$), such that the second bowl is nested within the first bowl while allowing extraction of the second bowl from the first bowl,
- wherein the third external length ($3l$) is less than the internal length ($1l$) in order to permit the third bowl to fit lengthwise within the first bowl, such that the third bowl is nested within the first bowl, while allowing extraction of the third bowl from the first bowl; and
- wherein the third external width ($3w$) is half or less than half of the internal width ($1w$).

7. The surgical bowl set of claim 6, which includes a fourth bowl nested in the third bowl and a fifth bowl nested in the fourth bowl.

8. The surgical bowl of claim 7, which also contains a sixth bowl that is configured to be nested within the second bowl.

9. The surgical bowl set of claim 6, in which the bowls each have a base and upstanding walls which taper outwardly towards a bowl opening, and a flange around the bowl opening.

10. The surgical bowl set of claim 6, in which the second and third bowls are of different heights, and features flanges that overlap on abutting respective sides.

* * * * *